(12) United States Patent
Lelental et al.

(10) Patent No.: US 9,933,421 B2
(45) Date of Patent: Apr. 3, 2018

(54) CATALYTIC MARKING NANOPARTICLES FOR ULTRASENSITIVE BIOASSAY APPLICATIONS

(71) Applicant: CatAssays, Rochester, NY (US)

(72) Inventors: Mark Lelental, Rochester, NY (US); Henry J. Gysling, Rochester, NY (US)

(73) Assignee: CatAssays, Rochester, NY (US)

( * ) Notice: Subject to any disclaimer, the term of this patent is extended or adjusted under 35 U.S.C. 154(b) by 340 days.

(21) Appl. No.: 13/970,107

(22) Filed: Aug. 19, 2013

(65) Prior Publication Data

US 2015/0050672 A1 Feb. 19, 2015

(51) Int. Cl.
| | |
|---|---|
| *B82Y 15/00* | (2011.01) |
| *G01N 33/543* | (2006.01) |
| *A61K 49/00* | (2006.01) |
| *G01N 33/58* | (2006.01) |
| *C12Q 1/68* | (2018.01) |
| *C12Q 1/26* | (2006.01) |
| *G01N 33/53* | (2006.01) |
| *G01N 33/84* | (2006.01) |

(52) U.S. Cl.
CPC ... *G01N 33/54346* (2013.01); *A61K 49/0091* (2013.01); *B82Y 15/00* (2013.01); *C12Q 1/26* (2013.01); *C12Q 1/682* (2013.01); *G01N 33/5308* (2013.01); *G01N 33/54313* (2013.01); *G01N 33/585* (2013.01); *G01N 33/587* (2013.01); *G01N 33/84* (2013.01)

(58) Field of Classification Search
CPC ........ C12Q 2563/137; C12Q 2563/155; A61K 47/48215; A61K 49/0093; A61K 49/0091; C08L 2203/02; B82Y 30/00; B82Y 15/00; C08G 65/2606; C08G 65/2609; C08G 65/2618; C08G 65/329; C08G 65/33337; C08G 65/33396; C08G 65/3356; G01N 33/5434; G01N 33/54313; G01N 33/54346; G01N 33/587
USPC ................ 977/773, 905, 918, 920, 924, 927
See application file for complete search history.

(56) References Cited

U.S. PATENT DOCUMENTS

| | | | | |
|---|---|---|---|---|
| 6,251,581 | B1 * | 6/2001 | Ullman ................ | C07D 265/30 252/582 |
| 2006/0003457 | A1 * | 1/2006 | Porter .................... | B82Y 15/00 436/56 |
| 2011/0014473 | A1 * | 1/2011 | Ying ........................ | B82Y 5/00 428/407 |
| 2011/0236989 | A1 * | 9/2011 | Suri .................... | G01N 21/6428 436/172 |
| 2012/0164749 | A1 * | 6/2012 | Luchini .............. | G01N 33/5432 436/177 |
| 2013/0315972 | A1 * | 11/2013 | Krasnow ................ | A01N 25/12 424/409 |

* cited by examiner

*Primary Examiner* — Erik B Crawford
(74) *Attorney, Agent, or Firm* — Hoffman Warnick LLC (57) ABSTRACT

Disclosed herein is a composition for ultrasensitive bioassay applications. The composition includes a plurality of dispersible, nanoparticles having a size less than 500 nm. The nanoparticles contain a metal catalyst or a metal catalyst precursor. The nanoparticles are conjugated to at least one biospecific binding reactant that is selectively reactive with a target analyte. The composition includes a dispersing medium. A method and a kit for conducting bioassays are described.

19 Claims, 2 Drawing Sheets

CATALYTIC MARKING NANOPARTICLES FOR ULTRASENSITIVE BIOASSAY APPLICATIONS

BACKGROUND

Field of Use

The disclosure herein relates to ultrasensitive bioanalytical assays based on the use of high-gain catalytic chemical amplification methods and catalytic nanoparticulate labeling reagents useful in such assays. The ultrasensitive bioanalytical assays of this invention utilize high gain catalytic chemical amplification methods to detect the presence and to quantify the concentrations of target analytes.

BACKGROUND

In the field of biological assays, methods are increasingly sought which allow the limits of detection and analysis of biological entities in biotic fluids to be decreased to lower concentrations, to obtain very high detection sensitivity. Thus, technological improvements include the instrumental environment, for example the limits for detecting a signal, but also the design of the sensor reagent itself. Improvements at the signal level have reached a threshold beyond which it is no longer possible to detect the biomolecules, such threshold being of the order of nanomolar (nM) or picomolar (pM).

Nonetheless, other improvements have enabled the signal to be measured owing to an amplification of the signal on which the detection principle relies. Such amplification finds its preferred application in the field of biological sensors given that the conditions implemented in biological analysis are compatible with bio-amplification systems. Currently, two bio-amplification modes are employed in systems intended to detect, for example, immunological reactions. According to a first amplification mode, in ELISA (Enzyme Linked Immunosorbant Assays) tests, the molecule to be detected, for example an antibody that interacts with a chemical entity such as an immobilized antigen, is chemically linked to an enzyme. The enzyme is used to catalyze a chemical reaction that provides the measured dye signal of the assay. In the currently used ELISA systems, the enzymes which catalyze the production of chemical entities are almost always hydrolases. The water soluble reaction products are preferably detected in the whole reaction medium by measuring a characteristic property such as absorption, luminescence or bioluminescence.

In biosensors, a second amplification mode is obtained by increasing the number or mass of species detected. This amplification principle is achieved, for example, by linking mass markers to the molecule to be detected. If the detection principle relies on fluorescence or absorption, fluorescent or absorbent molecules are chemically linked to the target chemical entity. By way of an example of this type of amplification, U.S. Pat. No. 5,175,270, incorporated in its entirety by reference here, discloses an amplification mechanism involving a dendrimer architecture at the surface of the sensor. The modified molecule link on each target molecule or the marked secondary reagent link (for example colloids, nanoparticles or fluorophore-labeled secondary antibodies) produce linear signal amplification. Latex microspheres, semiconductor nanocrystalline compounds or colloidal gold are mass markers currently used in biosensor systems. In commercial amplification systems, secondary antibodies strongly marked by fluorescent molecules contribute to increasing the signal in a linear manner.

Generally, the systems amplify the sensor signals via reactions catalyzed by an enzyme which increases the number of secondary chemical entities, typically an organic dye, in the medium by catalysis (catalytic amplification for global detection). Otherwise, the sensor signals are increased by adding mass, for mass sensitive detection, or by increasing the number of labeled molecules, which are linked to the unit.

By way of example of linear amplification at the surface of a sensor, fluorescent signal amplification may be cited. In this system the secondary antibodies are conjugated to a fluorophore to allow detection of targets in small quantities. These two amplification modes which have been briefly described above have allowed detection sensitivity to be substantially increased, either in solution or on a surface. They do not, however, allow a sufficiently high signal to be obtained to make them useful in practice for a number of medically significant bioassays for disease detection, especially in early stages where therapeutic intervention could significantly increase patient survival rates.

Binding-pair (also known as ligand-receptor, molecular recognition binding and the like) techniques play an important role in many applications of biomedical analyses and are gaining importance in the fields of environmental science, veterinary medicine, pharmaceutical research, food and water quality control and the like. For the detection of analytes at low concentrations (less than about 1 pM analyte/sample volume analyzed) the use of fluorescent, luminescent, chemiluminescent, or electrochemiluminescent labels and detection methods are often used.

For the detection of low concentrations of analytes in the field of diagnostics, the methods of chemiluminescence and electrochemiluminescence are gaining widespread use. These methods of chemiluminescence and electrochemiluminescence provide a means to detect low concentrations of analytes by further amplifying the chemical signal of the luminescent molecules many-fold, the resulting "signal amplification" then allowing for detection of low concentrations of analytes.

In addition, the method of Polymerase Chain Reaction (PCR) and other related techniques, have gained wide use for amplifying the number of nucleic acid analytes in the sample. By the addition of appropriate enzymes, reagents, and temperature cycling methods, the number of nucleic acid analyte molecules is amplified such that the analyte can be detected by most known detection means. The high level of commercial activity in the development of new signal generation and detection systems, and the development of new types of test kits and instruments utilizing signal and analyte molecule amplification attests to the importance and need for detection methods with improved sensitivity.

Thus, increased signal amplification for the detection of analytes is desirable.

SUMMARY

Disclosed herein is a composition for ultrasensitive bioassay applications. The composition includes a plurality of dispersible nanoparticles having a size less than 500 nm. The nanoparticles include a water-insoluble, water-swellable polymer. The nanoparticles contain a metal catalyst or a metal catalyst precursor. The nanoparticles are conjugated to at least one biospecific binding reactant that is selectively reactive with a target analyte. The composition includes a dispersing medium.

Described herein is a method for detecting and quantifying the presence of a target analyte of interest by a high gain redox chemical amplification having an amplification factor of about $10^7$ to about $10^9$. The method includes reacting nanoparticles with the target analyte to form a reaction mixture. The nanoparticles include a water-insoluble, water-swellable polymer. The nanoparticles have a size less than 500 nm. The nanoparticles contain a metal catalyst or a metal catalyst precursor. The nanoparticles are dispersed in a dispersing medium. The nanoparticles are conjugated to at least one biospecific binding reactant reactive with target analyte. The reaction forms a first reaction product including the metal catalyst or metal catalyst precursor contained in a reaction mixture. The reaction mixture is separated into two or more fractions. The first reaction product present in at least one of the two or more fractions is reacted with a high gain redox chemical amplification formulation, the high gain redox chemical amplification formulation including an oxidizing agent and a reducing agent to form a second reaction product in the form of a dye or a metal. The dye or metal is detected and quantified to determine the amount of the target analyte.

There is provided a kit for detecting and quantifying the presence of a target analyte of interest. The kit includes a plurality of nanoparticles having a size less than 500 nm, wherein the nanoparticles comprise a water-insoluble, water-swellable polymer, wherein the nanoparticles contain a metal catalyst or a metal catalyst precursor, and are conjugated to at least one biospecific binding reactant that is selectively reactive with a target analyte dispersed in a dispersing medium. The kit includes a high gain redox chemical amplification formulation comprising an oxidizing agent and a reducing agent, an ELISA plate and the ELISA bioassay reagents.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

It should be noted that some details of the figures have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. Wherever possible, the same reference numbers will be used throughout the drawings to refer to the same or like parts.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Illustrations with respect to one or more implementations, alterations and/or modifications can be made, by way of illustration, without departing from the spirit and scope of the appended claims. In addition, while a particular feature may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

In U.S. Pat. No. 7,820,394, incorporated by reference in its entirety herein, a method of high gain catalytic amplification to detect the presence of target analytes was described. Disclosed herein is a composition, method and kit for detecting and quantifying the presence of a target analyte of interest by a high gain redox chemical amplification reaction having an amplification factor of $10^7$ to $10^9$. The use of nanoparticles containing a metal catalyst precursor or metal catalyst and conjugated to a biospecific binding reactant that is selectively reactive with the target analyte of interest allows improved detection and quantification of the target analyte.

In the method of U.S. Pat. No. 7,820,394, the specific detection reagent was labeled with a metal catalyst or catalyst precursor. Such a method requires that a protocol for each specific detection reagent labeling process be developed for use in a bioassay. The process to prepare the specific detection reagent labeled with the metal catalyst or metal catalyst precursor while maintaining its ability to selectively bind to the target analyte of the assay is time consuming and expensive. The present invention provides a generic catalytic labeling reagent composition that can be readily incorporated in any assay.

The composition includes organic, inorganic or organic-inorganic composite marking nanoparticles. The nanoparticles contain a metal catalyst or a metal catalyst precursor. The nanoparticles are conjugated to a biospecific binding reactant that is selectively reactive with the target analyte of interest. The target analyte of interest is reacted with the biospecific binding reactant coupled to the nanoparticles to selectively form a first reaction product in a reaction mixture. The first reaction product includes the metal catalyst or the metal catalyst precursor. The first reaction product is separated from the reaction mixture into two or more fractions. The target analyte of interest is detected and quantified by subjecting said first reaction product present in at least one of the fractions to a high gain redox chemical amplification formulation comprising an oxidizing agent and a reducing agent to produce a second reaction product in the form of a dye or metal. The dye or metal is formed in a reaction catalyzed by said first reaction product. The high gain redox chemical amplification formulation includes one of the following redox combinations. A reducing agent and leuco dye that give dye signal on chemical reduction of leuco dye. An oxidizing agent and leuco dye that give a dye signal on chemical oxidation of leuco dye. A reducing agent and metal ion oxidant that on chemical reduction gives a metal signal. The choice of the chemical nature of reaction product (e.g., solvent soluble dye, solvent insoluble dye or solvent insoluble elemental metal) will be dictated by the specific assay of interest and the type of sample being analyzed.

Furthermore the disclosure herein is related to a diagnostic kit for ultrasensitive bioassay applications which comprises catalytic marking nanoparticles which are labeled with a metal catalyst or a metal catalyst precursor, and conjugated with at least one biospecific binding reactant and a high gain redox chemical amplification formulation comprising an oxidizing and a reducing agent and an ELISA plate and the ELISA bioassay reagents (e.g., capture and detection antibodies specific for the target disease biomarker, the blocking agent and buffers). A diagnostic kit includes a collection of chemical reagents and equipment for use in performing a diagnostic bioassay and can be put together for any specific purpose or organization. There is a wide variation in the contents of diagnostic bioassay kits based on the knowledge and experience of those putting it together, the differing bioassay requirements of the area where it may be used, and variations in legislation or regulation in a given area.

A diagnostic kit for ultrasensitive bioassay disclosed herein can include a dispersion of catalytic marking nanoparticles which contain a metal catalyst or a metal catalyst precursor, and conjugated with at least one biospecific binding reactant. The kit can include a dispersing medium and a dispersing aid or dispersion stabilizing agent. The kit can include a high gain redox chemical amplification formulation including a leuco dye or a reducible metal complex and a reducing agent, an ELISA plate and the ELISA bioassay reagents (e.g., capture and detection antibodies specific for the target disease biomarker, the blocking agent and buffers).

Nanoparticle-biospecific binding reactant conjugates are used for various purposes, including producing detectable signals in chemical and biological assays. The efficiency of bioconjugates in such processes is determined, at least in part, by the number of biomolecules that are conjugated to each nanoparticle and available for whatever a particular purpose requires. For example, and with reference to using protein nanoparticle conjugates for in-vitro diagnostics, one factor that determines bioconjugate efficiency is how many protein molecules are conjugated to a nanoparticle and available for binding target analyte molecules.

The nanoparticle-biospecific binding reactant conjugates disclosed herein include a nanoparticle having conjugated thereto at least one species of a biospecific binding reactant or multiple different biospecific binding reactants of the same class, or multiple biospecific binding reactants of different classes.

The disclosure herein can be applied to nanoparticle-biospecific binding reactant conjugates having any suitable biospecific binding reactant, including but not limited to, amino acids, peptides, proteins, haptens, nucleic acids, oligonucleotides, DNA, RNA, and combinations thereof. A single type of suitable biospecific binding reactant may be conjugated to the nanoparticle, more than one suitable biospecific binding reactant of a particular class may be conjugated to the nanoparticle, and two or more classes of suitable biospecific binding reactant molecules may be conjugated to the nanoparticle. Preferably, the biospecific binding reactant is selected from the group consisting of an antibody, an antigen, a receptor ligand, a specific binding protein, avidin, streptavidin, biotin, a nucleic acid, and a peptide.

Unless otherwise noted, technical terms are used according to conventional usage.

The term "dispersible" as used herein refers to essentially unaggregated particles in a dispersion medium, such that discrete particles of about 2 nm to about 500 nm can be sustained indefinitely at high concentrations without aggregation or precipitation.

The term "polymer" as used herein refers to a compound having two or more monomer units, and is intended to include linear and branched polymers. The term "branched polymer" includes simple branched structures, hyperbranched structures and dendritic polymers. Polymers herein may be naturally occurring, chemically modified, or chemically synthesized.

The term "composite material(s)" are material(s) made from two or more constituent materials with significantly different physical or chemical properties, that when combined, produce a material with characteristics different from the individual components. The individual components remain separate and distinct within the finished structure.

The term "polyelectrolyte" refers to a polymer that contains ionized or ionizable groups. The ionized or ionizable groups can be cationic or anionic. Examples of cationic groups include amino and quaternary ammonium groups, and examples of anionic groups include carboxylates, sulfonates and phosphates. The polyelectrolytes can be homopolymers, random polymers, alternate polymers, graft polymers, or block copolymers. The polyelectrolytes can be synthetic or naturally occurring. The polyelectrolytes can be linear, branched, hyper branched, or dendrimeric. Examples of cationic polymers include, but are not limited to, poly (allylamine hydrochloride) (PAAH), and poly (diallydimethylammonium chloride) (PDDA). Examples of anionic polymers include, but are not limited to, polyacrylic acid (PAA), poly (methacrylic acid), poly(sodium styrene sulfonate) (PSS), and poly(2-acrylamido-2-methyl-1-propane sulphonic acid) (PAMCS). In some embodiments, polymer includes a biopolymer, such as carboxymethylcellulose, chitosan, and poly (lactic acid). See, for example, U.S. Pat. Nos. 7,501,180 and 7,534,490, the entire contents of both are herein incorporated by reference.

The term "antibody" refers to immunoglobulins or immunoglobulin-like molecules, including by way of example and without limitation, IgA, IgD, IgE, IgG and IgM, and combinations thereof, and similar molecules produced during an immune response in any chordate such as a vertebrate, for example, in mammals such as humans, goats, rabbits and mice, and fragments thereof that specifically bind to a molecule of interest (or a group of highly similar molecules of interest) to the substantial exclusion of binding to other molecules. An "antibody" typically includes a polypeptide ligand having at least a light chain or heavy chain immunoglobulin variable region that specifically recognizes and binds an epitope of an antigen. Immunoglobulins are composed of a heavy and a light chain, each of which has a variable region, termed the variable heavy ($V_H$) region and the variable light ($V_L$) region. Together, the $V_H$ region and the $V_L$ region are responsible for binding the antigen recognized by the immunoglobulin. Exemplary immunoglobulin fragments include, without limitation, proteolytic immunoglobulin fragments, such as F(ab')$_2$ fragments, Fab' fragments, Fab'-SH fragments and Fab fragments, as are known in the art, recombinant immunoglobulin fragments, such as sFv fragments, dsFv fragments, bispecific sFv fragments, bispecific dsFv fragments, F(ab)'$_2$ fragments, single chain Fv proteins ("scFv"), and disulfide stabilized Fv proteins ("dsFv"). Other examples of antibodies include diabodies, and triabodies (as are known in the art), and camelid antibodies. "Antibody" also includes genetically engineered molecules, such as chimeric antibodies (for example, humanized murine antibodies), and heteroconjugate antibodies (such as, bispecific antibodies)

The term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

The term "epitope", also known as antigenic determinant, refers to the part of an antigen that is recognized by the immune system, specifically by antibodies, B cells, or T cells. The part of an antibody that recognizes the epitope is called a paratope. Although epitopes are usually non-self proteins, sequences derived from the host that can be recognized are also epitopes. The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. Most epitopes are conformational.

The term "biospecific binding reactant" refers to any molecule that may be included in a biological system, including but not limited to, a synthetic or naturally occurring protein, glycoprotein, lipoprotein, amino acid, nucleoside, nucleotide, nucleic acid, oligonucleotide, DNA, RNA, carbohydrate, sugar, lipid, fatty acid, hapten, an antibody, an antigen, a receptor ligand, a specific binding protein, avidin, streptavidin, biotin, a nucleic acid, a peptide and the like.

The term "avidin" refers to any type of protein that specifically binds biotin to the substantial exclusion of other small molecules that might be present in a biological sample. Examples of avidin include avidins that are naturally present in egg white, oilseed protein (e.g., soybean meal), and grain (e.g., corn/maize), and streptavidin, which is a protein of bacterial origin.

The term "nanoparticle-biospecific binding reactant conjugate" refers to a compound having a nanoparticle, and a biospecific binding reactant coupled to the nanoparticle, either directly or indirectly, by any suitable means. For example, the biospecific binding reactant can be covalently or noncovalently (e.g. electrostatically) coupled to the nanoparticle. Indirect attachment of the biomolecule to the nanoparticle also is possible, such as by using a "linker" molecule, so long as the linker does not negatively affect the catalytic activity of the labeled nanoparticle or the function of the biospecific binding reactant. The linker preferably is bio-compatible. Common molecular linkers known in the art include a primary amine, a thiol, streptavidin, neutravidin, biotin, or similar compounds.

The terms "conjugating", "joining", "bonding" and "linking" refer to coupling a first unit to a second unit. This includes, but is not limited to, covalently bonding one molecule to another molecule, covalently or noncovalently bonding one molecule to another (e.g. electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, adsorption, grafting, solid state synthesis and any and all combinations of such couplings.

The term "detectable label" refers to a detectable compound or composition that is attached directly or indirectly to another molecule, such as an antibody or a protein, to facilitate detection of that molecule. Suitably functionalized nanoparticles can provide one, non-limiting example of a class of detectable labels.

The term "nanoparticle(s)" refers to particles having spherical, non-spherical, dendridic or tubular morphology, with a size measured in nanometers, for example, a nanoparticle that has the size of a largest dimension of less than about 500 nm, or in embodiments less than about 150 nm. Examples of nanoparticles include, by way of example and without limitation; inorganic particles, organic particles or organic-inorganic composite particles. Nanoparticles can be electrically conductive insulating or semi-conductive. Nanoparticles can be metallic or polymeric. Nanoparticles can be amorphous, crystalline, partially crystalline or polycrystalline. Nanoparticles can be substantially homogeneous in material properties, or in certain embodiments can be heterogeneous (e.g. heterostructures such as core-shell structures, etc.). Nanoparticles can be fabricated from essentially any convenient material or materials. Nanoparticles can include pure materials, substantially pure materials, doped materials and the like. Nanoparticles having a core-shell structure include an inner core of a inorganic or organic material, which can be a polymer or extended network structure and polymeric shell disposed on the core. The shell can be solvent insoluble, water-insoluble and water-swellable. The shape of the nanoparticles can vary. For example, generally spherical morphologies (such as solid beads, microbeads, or hollow spheres), can be used, as well as particles that are cubic, plate-like, tubular or acicular (elongated or fibrous). Additionally, the nanoparticles can have an internal structure that is hollow, porous or void free, or a combination of any of the foregoing, e.g., a hollow center with porous or solid walls such as carbon nanotubes and inorganic tubular structures as Halloysite which has the general formula $Al_2Si_2O_5(OH)_4$. Nanoparticles can be formed from polymeric and/or non-polymeric inorganic materials, polymeric and/or non-polymeric organic materials, organic-inorganic composite materials, as well as mixtures of any of the foregoing. Additionally, as used herein, the term "polymer" is meant to encompass oligomers, and includes without limitation both homopolymers and copolymers.

The term "core-shell nanoparticles" refers to nanoparticles including a nanoparticle core and a shell layer. The nanoparticle core can be inorganic, organic or organic-inorganic composite. The average particle size of core particles related to the present invention is from about 1 nm to about 500 nm to about 1 nm to 149.5 nm. In embodiments, the shell layer includes a solvent-insoluble polymer, water-insoluble polymer and water-swellable polymer. The shell layer has a thickness in the range from about 0.5 nm to about 249.5 nm, or in embodiments from about 1.0 nm to about 74.5 nm.

The term "organic material," as used herein, means carbon containing compounds wherein the carbon atoms are typically bonded to one or more carbon atoms or hydrogen atoms.

As used herein, the "inorganic material" is any material that is not an organic material.

As used herein, the term "composite material" means a combination of two or more differing materials. More specifically, the surface of the particle can be modified in any manner well known in the art, including, but not limited to, chemically or physically changing its surface characteristics using techniques known in the art, such as treatment with an oxidizing or reducing agent solution, treatment with an acid or base solution, or plasma surface modification processes.

As aforementioned, the nanoparticles can include inorganic materials known in the art. Suitable particles can be formed from ceramic materials, oxide materials, chalcogenide materials, metallic materials, and mixtures of any of the foregoing. Non-limiting examples of such ceramic materials can comprise metal oxides, mixed metal oxides, metal nitrides, metal carbides, metal sulfides, metal silicates, metal borides, metal carbonates, and mixtures of any of the foregoing. A specific, non-limiting example of a metal nitride is boron nitride; a specific, non-limiting example of a metal oxide is zinc oxide; non-limiting examples of suitable mixed metal oxides are aluminum silicates and magnesium silicates; Perovskite ($CaTiO_3$), Spinel ($MgAl_2O_4$), Delaffosite ($CuFeO_2$) and structurally related inorganic phases, non-limiting examples of suitable metal sulfides are molybdenum disulfide, tantalum disulfide, tungsten disulfide, and zinc sulfide; non-limiting examples of metal silicates are aluminum silicates and magnesium silicates, such as vermiculite.

In certain embodiments, the nanoparticles may comprise inorganic materials selected from aluminum, barium, bismuth, boron, cadmium, calcium, cerium, cobalt, copper, iron, lanthanum, magnesium, manganese, molybdenum, nitrogen, oxygen, phosphorus, selenium, silicon, silver, sulfur, tin, titanium, tungsten, vanadium, yttrium, zinc, and zirconium, including oxides thereof, nitrides thereof, phosphides thereof, phosphates thereof, selenides thereof, sulfides thereof, sulfates thereof, and mixtures thereof. Suitable non-limiting examples of the foregoing inorganic nanoparticles include alumina, silica, titania, ceria, zirconia, bismuth oxide, magnesium oxide, iron oxide, aluminum silicate, boron carbide, nitrogen doped titania, and cadmium selenide.

The nanoparticles can include, for example, a core of essentially a single inorganic oxide, such as silica in colloidal, fumed, or amorphous form, alumina or colloidal alumina, titanium dioxide, iron oxide, cesium oxide, yttrium oxide, colloidal yttria, zirconia, e.g., colloidal or amorphous zirconia, and mixtures of any of the foregoing; or an inorganic oxide of one type upon which is deposited an organic oxide of another type.

Non-polymeric, inorganic materials useful in forming the nanoparticles used in the present invention can comprise inorganic materials selected from, metals, oxides, carbides, nitrides, borides, sulfides, silicates, carbonates, sulfates, and hydroxides. A non-limiting example of a useful inorganic oxide is zinc oxide. Non-limiting examples of suitable inorganic sulfides include molybdenum disulfide, tantalum disulfide, tungsten disulfide, and zinc sulfide. Non-limiting examples of useful inorganic silicates include aluminum silicates and magnesium silicates, such as vermiculite. Non-limiting examples of suitable metals include molybdenum, platinum, palladium, nickel, aluminum, copper, gold, iron, silver, alloys, and mixtures of any of the foregoing.

In certain embodiments, the nanoparticles can be selected from fumed silica, amorphous silica, colloidal silica, alumina, colloidal alumina, titanium dioxide, iron oxide, cesium oxide, yttrium oxide, colloidal yttria, zirconia, colloidal zirconia, and mixtures of any of the foregoing. In certain embodiments, the nanoparticles comprise colloidal silica. As disclosed above, these materials can be surface treated or untreated. Other useful particles include surface-modified silicas, such as are described in U.S. Pat. No. 5,853,809, incorporated in its entirety by reference herein. A dispersion of silver halide stabilized with cross-linked gelatin, well known in the photographic art, is an example of such nanoparticles.

The nanoparticles can be formed from non-polymeric, organic or organometallic materials. Non-limiting examples of non-polymeric, organic materials include, but are not limited to, stearates (such as zinc stearate and aluminum stearate), diamond, carbon black and stearamide.

The nanoparticles can also be hollow particles formed from materials selected from polymeric and non-polymeric inorganic materials, polymeric and non-polymeric organic materials, composite materials and mixtures of any of the foregoing The nanoparticles used in the present invention can be formed from inorganic polymeric or composite materials. Non-limiting examples of useful inorganic polymeric materials include polyphosphazenes, polysilanes, polysiloxanes, polygermanes, polymeric sulfur, polymeric selenium, silicones and mixtures of any of the foregoing.

Mixtures of any of the previously described polymeric, composite, inorganic and/or organic nanoparticles can also be used.

The term "catalytic marking nanoparticles which are labeled with a metal catalyst or a metal catalyst precursor" refers to the nanoparticles containing a metal catalyst or a metal catalyst precursor conjugated, coupled, bound or bonded either directly or indirectly by any suitable means to the surface or within the volume of the nanoparticles. For example, the metal catalyst or a metal catalyst precursor can be covalently or non-covalently (e.g. electrostatically) coupled to the nanoparticles. The critical property of the nanoparticles containing a metal catalyst or a metal catalyst precursor and conjugated to at least one biospecific binding reactant that is selectively bound to the target analyte is that the active catalyst for the assay signal generating redox amplification process is accessible to the solution comprising the amplification system.

Examples of nucleic acids include genes (e.g., a gene associated with a particular disease), viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids, etc.

The term "polypeptide" refers to a polymer in which the monomers are amino acid residues which are joined together through amide bonds. When the amino acids are alpha-amino acids, either the L-optical isomer or the D-optical isomer can be used. The terms "polypeptide" or "protein" as used herein encompass any amino acid sequence and include modified sequences such as glycoproteins. Polypeptide includes naturally occurring proteins, as well as those which are recombinantly or synthetically produced. "Residue" or "amino acid residue" includes an amino acid that is incorporated into a protein, polypeptide, or peptide.

The term "protein" refers to a molecule comprised of amino acids. The distinction between peptides and proteins typically involves size or length; that is peptides are shorter than proteins. There are several different conventions used to determine if a molecule is a peptide or a protein. For purposes herein, in order for a polypeptide to be a protein, it typically has some in-vivo biological function. Another convention places an informal dividing line at approximately 50 amino acids, i.e. amino acid chains having 50 or fewer amino acids are peptides, and chains having 51 or more amino acids are proteins. Because of the arbitrary nature of this definition, a person of ordinary skill in the art might also consider that peptides are amino acid polymers that do not have a defined secondary structure, whereas proteins have defined secondary structures. By this definition, the same molecule can be either a peptide or a protein depending on its environment.

The term "purified" does not require absolute purity; rather, it is intended as a relative term. Thus, for example, a purified peptide, protein, conjugate, or other compound is one that is isolated in whole or in part from proteins or other constituents of a mixture. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Biospecific Binding Reactant Conjugates

Biospecific binding reactants can be conjugated to any nanoparticle to form nanoparticle-biospecific binding reactant conjugate within the scope of the present invention. Nanoparticles can be selected for a particular purpose, such as for producing a detectable signal. Exemplary nanoparticles include, without limitation, inorganic or organic or organic-inorganic composite materials which can be electrically conductive, insulating, semiconductive, polymeric, metal or metal alloy nanoparticles or nanoclusters. Suitable functional biomedical nanoparticle morphologies include nanorods, nanotubes, nanowires, nanowire self assemblies, nanospheres and dendridic structures. Nanoparticles having a core-shell structure include an inner core of a inorganic or organic material which can be electrically conductive insulating, semiconductive, metallic or a polymeric material; and solvent-insoluble, water-insoluble and water-swellable polymeric shell provided thereon.

The present invention is directed to all potential biomolecules that may be conjugated to a nanoparticle. For most applications, the biomolecule(s) is/are an amino acid/peptide/protein or nucleoside/nucleotide/nucleic acid. Specific exemplary biomolecules useful for providing the bioconjugates of the present invention include, without limitation: monoclonal or polyclonal antibodies, such as IgA, IgD, IgE, IgG, IgM; antibody fragments that specifically bind to a molecule of interest (or a group of highly similar molecules of interest) to the substantial exclusion of binding to other molecules including, without limitation, proteolytic antibody fragments [such as F(ab')$_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, F(ab)'$_2$ fragments, single chain Fv proteins ("scFv"), and disulfide stabilized Fv proteins ("dsFv"). Other useful biomolecules include diabodies, triabodies, and camelid antibodies; genetically engineered antibodies, such as chimeric antibodies, for example, humanized murine antibodies); heteroconjugate antibodies (such as, bispecific antibodies); streptavidin; receptors; enzymes; BSA; polypeptides; aptamers; and combinations thereof.

Preparation of Nanoparticle-Biospecific Binding Reactant Conjugates

Nanoparticle-biospecific binding reactant conjugates, are commercially available. Methods for making nanoparticle-biospecific binding reactant conjugates are generally known in the art, and nanoparticle-biospecific binding reactant conjugates can be made by any suitable method known in the art. Exemplary methods for making nanoparticle-biospecific binding reactant conjugates are summarized below.

Peptide/Protein-Nanoparticle Conjugates

Exemplary methods for making protein-nanoparticle-biospecific binding reactant conjugates are disclosed in various United States patents, such as U.S. Pat. No. 6,592,844 incorporated in its entirety by reference herein. One method disclosed concerns mixing an aqueous solution of at least one protein or modified protein with an aqueous solution of at least one α-hydroxy acid or analogue or derivative thereof, adding to the mixture a coacervation agent, which results in the formation of microspheres incorporating the protein or modified protein, removing the coacervation agent, and recovering microspheres from the aqueous solution.

Nucleic Acid-Nanoparticle Conjugates

Oligonucleotide conjugates are disclosed in a number of issued U.S. patents, including U.S. Pat. Nos. 6,495,324, 6,750,016 and 6,767,702 incorporated in their entirety by reference herein. According to the '702 patent, nanoparticles, oligonucleotides or both are functionalized in order to attach the oligonucleotides to the nanoparticles, according to methods known in the art. For instance, oligonucleotides functionalized with alkanethiols at their 3'-termini or 5'-termini readily attach to gold nanoparticles. The alkanethiol method also can be used to attach oligonucleotides to other metal, semiconductor and magnetic colloids and to the other nanoparticles listed above. Other functional groups for attaching oligonucleotides to solid surfaces include: phosphorothioate groups and substituted alkylsiloxanes; disulfides; sulfolanes and sulfoxides; isonitriles; silanes; phosphates; and combinations thereof.

Polymeric Nanoparticles

The polymeric nanoparticles of this invention are desirably formed by a water-swellable, water-insoluble polymer or combination of polymers. As used herein, the term "water-swellable, water-insoluble" refers to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles. As used herein, a material will be considered to be water soluble when it substantially dissolves in excess water to form a solution, thereby losing its initial, typically particulate, form and becoming essentially molecularly dispersed throughout the solvent. As a general rule, a water-soluble material will be free from a substantial degree of crosslinking, as crosslinking tends to render a material water-insoluble. As such, the water-swellable, water-insoluble polymer needs to be able to be effective to provide a desired amount of liquid-absorbing capacity, the ability of the redox amplification solution to access the active catalyst incorporated in the polymeric matrix being necessary to achieve a high assay signal.

The Polymer

One property of the water-swellable, water-insoluble polymer that is relevant to its effectiveness in providing a desired amount of liquid-absorbing capacity to the absorbent composition is its molecular weight. In general, a water-swellable, water-insoluble polymer with a higher molecular weight will exhibit a higher liquid-absorbing capacity as compared to a water-swellable, water-insoluble polymer with a lower molecular weight. A water-swellable, water-insoluble polymer having a relatively high molecular weight is often beneficial for use in the present invention. Nonetheless, polymers having a wide range of molecular weights are generally suitable for use herein. Water-swellable, water-insoluble polymers disclosed herein will beneficially have a weight average molecular weight greater than about 100,000, more beneficially greater than about 200,000, suitably greater than about 500,000, more suitably greater than about 1,000,000, and up to about 10,000,000. Methods for determining the molecular weight of a polymer are generally well known in the art. The water-swellable polymer will generally be cross-linked to provide water-insolubility. The amount of crosslinking should generally be above a minimum amount sufficient to make the polymer water-insoluble but also below some maximum amount so as to allow the polymer to be sufficiently water swellable so that the water-swellable, water-insoluble polymer absorbs a desired amount of liquid. The water-swellability and permeability of the water insoluble polymer provides for rapid access of the redox amplification solution of the bioassay to the catalyst or catalyst precursor species immobilized within the polymer.

Crosslinking of the polymer may generally be achieved by different types of crosslinking agents. The one type of crosslinking agent is a polymerizable crosslinking agent. Suitable polymerizable crosslinking agents are generally reactive to the monomer or monomers used to prepare the polymer and, thus, generally include at least two functional groups that are capable of reacting with the monomers. Examples of suitable polymerizable crosslinking agents include ethylenically unsaturated monomers, such as N,N'-methylene bis-acrylamide, for free radical polymerization, and polyamines or polyols for condensation polymerization.

The water-swellable, water-insoluble polymer useful in the composition described herein will either be acidic or basic in nature.

Suitable acidic water-swellable, water-insoluble polymers will include functional groups that are capable of acting as acids. Such functional groups include, but are not limited to, carboxyl groups, sulfate groups, sulfite groups, thiol groups and phosphate groups. In embodiments, the functional groups are carboxyl groups. Generally, the functional groups are attached to a crosslinked base polymer. Suitable base polymers include polyacrylamides, polyvinyl alcohols, ethylene maleic anhydride copolymers, polyvinylethers, polyacrylic acids, polyvinylpyrrolidones, polyvinylmorpholines, copolymers thereof and polyelectolytes, The polyelectrolytes can be linear, branched, hyper branched, or dendrimeric. Examples of cationic polymers include, but are not limited to, poly(allylamine hydrochloride) (PAAH), and poly(diallydimethylammonium chloride) (PDDA). Examples of anionic polymers include, but are not limited to, polyacrylic acid (PAA), poly(methacrylic acid), poly (sodium styrene sulfonate) (PSS), and poly(2-acrylamido-2-methyl-1-propane sulphonic acid) (PAMCS). Natural based polysaccharide polymers may also be used and include carboxymethyl celluloses, carboxymethyl starches, hydroxypropyl celluloses, algins, alginates, carrageenans, acrylic grafted starches, acrylic grafted celluloses, and copolymers thereof. Synthetic polypeptides can also be used such as polyaspartic acid and polyglutamic acid. Copolymers and mixtures of the above can also be used.

The acidic, water-swellable, water-insoluble polymer generally needs to be in its free acid form. In general, it is desired that the acidic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its acidic functional groups in free acid form. Alternatively, the acidic, water-swellable, water-insoluble polymer should not be substantially neutralized when used in the nanoparticle composition of the present invention. In general, it is desired that the acidic, water-swellable, water-insoluble polymer have a degree of neutralization of its acidic functional groups that is beneficially less than about 50 molar percent, more beneficially less than about 30 molar percent, suitably less than about 20 molar percent, more suitably less than about 10 molar percent, and most suitably substantially about 0 molar percent.

Desired acidic polymers include, ethylene maleic anhydride copolymer, acrylic acid grafted starch, acrylic acid grafted cellulose, carboxymethyl cellulose, and polyacrylamide methylpropane sulfonic acid. Most desired acidic water-swellable, water-insoluble polymers include polyacrylic acid, polyacrylamide methylpropane sulfonic acid, and acrylic acid grafted starch.

Suitable basic, water-swellable, water-insoluble polymers will contain functional groups that are capable of acting as bases. Such functional groups include, but are not limited to, primary, secondary, or tertiary amino groups, imino groups, imido groups, and amido groups. Suitably the functional groups are amino groups. Generally, the functional groups are attached to a crosslinked base polymer. Suitable base polymers include polyamines, polyethyleneimines, polyacrylamides, polydiallyl dimethyl ammonium hydroxide, and polyquaternary ammoniums. Natural based polysaccharide polymers may also be used and include chitin and chitosan. Synthetic polypeptides can also be used such as polyasparagines, polyglutamines, polylysines, and polyarginines. Mixtures and copolymers of the foregoing can also be used.

The basic, water-swellable, water-insoluble polymer generally needs to be in its free base form. In general, it is desired that the basic, water-swellable, water-insoluble polymer beneficially have at least about 50 molar percent, more beneficially at least about 70 molar percent, suitably at least about 80 molar percent, more suitably at least about 90 molar percent, and most suitably substantially about 100 molar percent of its basic, functional groups in free base form. Alternatively, the basic, water-swellable, water-insoluble polymer should not be substantially neutralized when used in the absorbent composition of the present invention. In general, it is desired that the basic, water-swellable, water-insoluble polymer have a degree of neutralization of its basic functional groups that is beneficially less than about 50 molar percent, more beneficially less than about 30 molar percent, suitably less than about 20 molar percent, more suitably less than about 10 molar percent, and most suitably substantially about 0 molar percent.

Desired basic water-swellable, water-insoluble polymers useful in the invention include chitosan, quaternary ammoniums, polyvinylamine, polyethylene imine, and polydialkylaminoalkyl methacrylamide. Most desired basic water-swellable, water-insoluble polymers useful in the invention include quaternary ammoniums, polyvinylamine, and polyethylene imine.

Another desired water-swellable, water-insoluble polymer useful in the invention is crosslinked gelatin. Gelatin is manufactured from protein collagen. The primary collagen sources for gelatin are animal hides and bones. Natural gelatin is usually a complicated mixture with many polypeptides of different molecular weight. Gelatin can also be prepared through genetic recombination engineering, and the gelatin by this method has precise molecular weight, isoelectric point, and molecular structure which can be designed according to specific applications. Gelatin exhibits a significant water solubility, therefore for the applications described herein, physical crosslinking or chemical crosslinking of gelatin is necessary. Dehydrogenation heat treatment and UV radiation are common methods for physical crosslinking, but their crosslinking efficacy is low and also uncontrollable. Chemical crosslinking has relatively higher efficacy. The common chemical crosslinkers include formaldehyde, glutaric dialdehyde, polyfunctional group epoxy crosslinker, polyfunctional group isocyanate crosslinker, acid azid diazoimido compounds and carbodiimide etc.

Metal Catalyst or Metal Catalyst Precursor

The term "metal catalyst" denotes a metal in its elemental form or a combination of such metals that interact with the assay signal generating redox amplification chemistry to reduce the activation energy for initiation of the amplification chemical reactions.

The term "metal catalyst precursor" denotes the metal salt, coordination or organometallic compound or combination of metal compounds, which is converted to the active metal catalyst in-situ by chemical reactions or by physical transformations.

The nanoparticles described herein must include a metal catalyst or a metal catalyst precursor of some type. For example, one or more metal-containing catalytically active particles or metal nuclei or their chemical precursors can be used. The metal catalyst-providing component can be any metal, especially transition metals including alloys with other transition metals, group 14, 15 or 16 periodic table main group elements, mixtures of such metals, metal binary compounds or metal salts or complexes that function as the desired redox catalyst, or provide the desired catalytically active nuclei by means of some chemical transformation of a catalyst precursor. The concentration of metal catalyst component can be from about 0.0001 to about 1.0 mole of metal compound per mole of oxidizing agent in the oxidation-reduction combination that gives the readable signal with the preferred range being from about 0.001 to about 0.1 mole of metal compound per mole of oxidizing agent.

Palladium metal nuclei are preferred catalysts since they provide useful catalytic sites that promote formation of the readable chemical signal which is the product of the catalytic amplification reaction (e.g., typically a transition metal such as Cu or Ni or a main group element such as tellurium, or an organic or organometallic dye). Other nuclei for promoting this process can alternatively be employed as catalysts. Such nuclei include chromium, iron, cobalt, nickel, copper, selenium, silver, tin, tellurium, iridium, ruthenium, rhenium, platinum, manganese, rhodium, and gold. Copper, silver, gold nickel, palladium, platinum, manganese, cobalt, rhodium, iridium are preferred. The catalytic nuclei can be in the form of small clusters of the metal, $M_n$ (n is ideally from about 2 to about 100) or present as metal binary compounds, such as phosphides, sulfides, selenides, tellurides, oxides or the like. The palladium catalyst can be incorporated in the process of this invention as preformed metal clusters or aggregates or the clusters or aggregates of the active catalyst can be provided from any convenient precursor source, such as compounds that are decomposable through various means to the desired metal nuclei. Such decomposable compounds include, but are not limited to, $K_2[Pd(C_2O_4)_2]$, $PdCl_2$, $K_3[Co(C_2O_4)_3]$, $K_2[MCl_4]$ wherein M is Pd or Pt, $[Et_4N]_2[MCl_4]$ wherein M is Pd or Pt, $[M(PR_3)_2Cl_2]$ wherein M is Pd or Pt, R is alkyl or aryl, $[M(acac)_2(CO)_2]$ wherein M is Rh or Ir, "acac" is acetylacetonate; $[Co(NH_3)_5N_3]Cl_2$, $Se(S_2CO\text{-iso-}C_3H_7)_2$, $Te[S_2P(OCH_3)_2]_2$, $K_2[Pt(C_2O_4)_2]$, $[Pd[P(C_6H_5)_3]_2(C_2O_4)]$, $\{Cu[P(OCH_3)_3]_4\}B(C_6H_5)_4$, $\{Cu[P(OCH_3)_3]_2BH_3CN\}_2$, $\{Cu[Sb(C_6H_5)_3]_3Cl\}$ and $[Cu(\text{ethylenediamine})_2][B(C_6H_5)_4]_2$. Such catalyst precursor compositions can be converted to the active catalyst for the chemical amplification reaction by various means well know in the art, such as chemical reduction or exposure to actinic radiation such, as UV radiation or visible region light, or by heating to a suitable temperature.

Binary combinations of these metals are also efficient initiators or catalysts for the amplification chemistries disclosed herein because of their high degree of catalytic activity. Other metal-containing catalytically active compounds or catalyst precursors that can initiate amplification reactions are also useful for forming readable assay signals according to the invention. Other metal compounds that provide catalytic nuclei that are useful include chromium, iron, cobalt, nickel, copper, selenium, palladium, silver, tin, tellurium, iridium, ruthenium, rhenium, platinum, rhodium and gold compounds and combinations of these compounds. In still another embodiment, the metal catalyst precursor, for example a Pd(II) or Pt(II) compound, is spontaneously reduced to the catalytically active elemental metal by the reducing agent of the redox chemistry used as the chemical amplification element that provide the assay signal.

Dispersing Medium

As used herein, the term "aqueous," "aqueous phase," "aqueous medium," and the like, refers to a medium that either includes exclusively water or predominantly water in combination with another material such as, for example, an inert organic solvent. In certain embodiments, the amount of organic solvent present in the aqueous dispersions is less than 20 weight percent, with the weight percent being based on the total weight of the dispersion. Non-limiting examples of suitable organic solvents are propylene glycol monobutyl ether, ethylene glycol monohexyl ether, ethylene glycol monobutyl ether, ethanol, n-butanol, benzyl alcohol, and mineral spirits.

As used herein, the term "nonaqueous," "nonaqueous phase," "nonaqueous medium," and the like, refers to a medium that includes exclusively an organic solvent or predominantly an organic solvent in combination with water. In certain embodiments, the amount of water present in the nonaqueous medium of the present invention is less than 50 weight percent, with the weight percent being based on the total weight of the dispersion.

Dispersing Aid

As used herein the term "dispersing aid" refers to a surfactant which is usually an organic compound that is amphiphilic, meaning it contains both hydrophobic groups and hydrophilic groups. Such dispersing aids, which stabilize the nanoparticles and prevent aggregation and precipitation, are well known in the art.

The term "redox" denotes a composition or reaction comprising an oxidizing agent and a reducing agent. The term "visualization redox reaction" denotes a reduction-oxidation reaction in which the reaction product can be directly observed or measured based on one of its properties such as, for organic or organometallic dyes their optical density, or radiation emission produced on appropriate activation or excitation, such as by measurement of luminescence, phosphorescence, etc. In the case of metallic redox amplification products, signal measurement can be based on reflectance, conductivity, magnetic susceptibility or other metal property known in the art.

HIGH-Gain Catalytic Chemical Amplification Chemistry

The chemistry disclosed herein provides a readable signal related to the presence and concentration of the target analyte and includes two essential components: a catalyst or catalyst precursor and catalytic redox chemistry (i.e., a reaction pair comprising an oxidizing agent and a reducing agent). Each of these components can also have more than one component, as will be evident from the following discussion.

The "catalytic redox" chemistry includes one or more components that can be transformed or reacted in some manner in response to the ability of the catalyst to provide a readable signal. There are a number of types of precursor chemistries that can be used to provide an assay signal and a number of such chemistries are described in more detail below.

While a number of such chemistries are described below in relation to certain embodiments of the methods of this invention, it is understood that a skilled worker in the art would readily identify other useful amplification chemistries that would produce readable chemical signals within the spirit and scope of the present invention.

Oxidation-Reduction Amplification Chemistry

The preferred amplification chemistries which produce readable chemical signals useful in the practice of this invention are based on oxidation-reduction systems. Several such chemistries are described below in more detail.

Co (III) Systems

There are a number of known Co (III) imaging systems which can be utilized. In one type of a redox amplification system, Co (III) coordination complexes described below can be reduced in the presence of a reducing agent (such as those described below for the tellurium imaging systems). Cobalt (2+) compounds, generated by chemical reduction of such Co (III) compounds, are useful catalysts for the initiation of such amplification systems. In a second Co (III) imaging system, a Co (III) ligand compound is chemically reduced to a labile Co (II) complex, which can then readily undergo ligand substitution with another ligand present in the matrix to form a more stable Co(III) Lewis base compound with the liberation of the initial ligands bound to the Co(III) starting complex. For example, $[Co(NH_3)_6]^{3+}$, $[Co(ethylenediamine)_3]^{3+}$ and related Co(III) complexes can be used as image precursor chemistry to undergo catalytic ligand exchange and eventually provide stable and readable Co(III) coordination compounds. Ammonia or other amines are also released during this reaction and can be used to provide useful chemical signals, for example to form a dye from a pH-sensitive dye precursor or to activate a pH-sensitive reducing agent that can then be used in a variety of redox amplification systems. Co (2+) is a catalyst for such ligand exchange reactions of Co (3+)-ligand compounds useful in such amplification chemistries.

Silver-Based Redox Amplification Systems

Useful catalytic high-gain amplification chemistry can also be composed of an oxidant comprising a non-photosensitive silver (I) compound in combination with a reducing agent, and a metal nuclei catalyst (or catalyst precursor) as described below. Such silver (1+) compounds are well known in the art for use in thermographic and photothermographic imaging materials as non-photosensitive reducible silver sources. They include, but are not limited to, silver salts of thiones, triazoles, tetrazoles, imidazoles, and organic acids (fatty carboxylic acid containing 10 to 30 carbon atoms), silver salts of compounds containing mercapto or thione groups and derivatives (such as salts of mercaptotriazoles, mercaptobenzimidazoles and thioglycolic acids), silver salts of compounds containing an imino group (such as salts of benzotriazoles and imidazoles), silver salts of acetylenes, and mixtures of any of these silver salts. There are numerous publications describing such silver complexes, including U.S. Pat. No. 5,939,249, all incorporated herein by reference in its entirety. Compounds which are useful silver salt oxidizing agents include, but are not limited to, silver behenate, silver stearate, silver oleate, silver laurate, silver hydroxystearate, silver caprate, silver myristate and silver palmitate.

The silver compounds act as oxidizing agents and therefore must be used in combination with one or more reducing agents that can reduce silver (1+) ion in such compounds to metallic silver. A wide range of reducing agents are known for this purpose including, but not limited to, phenidone, hydroquinones, catechol, hindered bisphenols, amidoximes, hydrazides, ascorbic acid (and derivatives) and other classes of materials described, for example, in U.S. Pat. No. 5,939,249 (noted above).

The catalysts (or catalyst precursors) used with the noted silver compounds and reducing agents are transition metals or transition metal binary nuclei as described below.

Non-Silver High Gain Redox Amplification Systems

Similar to the silver compounds described above, a number of other metal compounds can act as oxidizing agents in thermal chemical amplification elements. Such compounds include salts or complexes of copper (II), copper (I), nickel (II), manganese (II) or (III), iron (II) or (III) and any other metal ion that can be reduced in the presence of the noted reducing agents. The metals are generally complexed with Lewis bases or ligands that are well known in the art including, but not limited to halides, pseudohalides, pyrophosphates, alkanolamines, carboxylic acids, organic amines, alkoxides, aryloxides, sulfur ligands such as thiolates, xanthates, dithiocarbamates, dithiophosphates or dithiophosphinates, and organophosphines such as triphenylphosphine and tri (p-tolyl)phosphine, and other ligands well know in the art.

Reducing agents useful in these high gain redox amplification systems include amine boranes such as dimethylamine borane, diethylamine borane, triethylamine borane, phosphine boranes such as $PAr_3BH_3$ (wherein Ar is an aryl such as phenyl, p-tolyl, etc.) and pyridine borane, borohydrides such as $C[BH_4]$ (wherein C is a cation such as sodium, potassium, a tetraalkylammonium cation such as tetraethylammonium or tetraphenylphosphonium), $NaBH_3CN$, $Na_2B_{10}H_{10}$, hydrazine and substituted hydrazine derivatives, sodium hypophosphite, sodium sulfite and organic reducing agents that are well known in the synthetic chemical, electroless plating and photographic art.

Examples of other heavy metal salt oxidizing agents are gold stearate, mercury behenate and gold behenate. Catalysts useful in this imaging system include the metal nuclei described below as well as binary compounds such as sulfides, borides and phosphides (such as $Cu_3P$, $CuP_2$, NiP, NiB, CoB, NiS, CuS, PdS and PtS).

Single Component ("Molecular") Redox Amplification

Still another type of chemical amplification element useful herein includes certain metal complexes which incorporate both the metal ion oxidant and the reducing agent (as a ligand) in a single molecular metal compound or complex. Such metal complexes may include more than one type of complexing ligand including ligands that stabilize the molecule before the catalytic redox amplification reaction. Examples of such useful molecular amplification elements include, but are not limited to, metalloboranes such as [Cu(PPh$_3$)$_2$BH$_4$], [Cu{P(OPh)$_3$}$_2$B$_3$H$_8$], [Cu(PPh$_3$)$_2$B$_9$H$_{13}$X] (wherein X is H, NCS, NCSe, NCBPh$_3$, NCBH$_3$, or NCBH$_2$NCBH$_3$), [Ag(PPh$_3$)$_2$BH$_4$] and [Mn(CO)$_5$B$_3$H$_8$] as well as those known in the art. Other useful molecular physical developers are metal xanthates such as Te(S$_2$COR)$_2$ wherein R can be a substituted or unsubstituted alkyl or aryl group and those described in the art. Still other useful molecular redox amplification compositions are metal complexes having the formula ML$_n$, wherein L is a 1,1-dithio ligand, M is a suitable metal ion (such as Te, Se, Cu, Cr, Mn, Co, Fe, Ni, Ag or Bi), and n is an integer of 1 to 4. Examples of such useful metal complexes with 1,1-dithio ligands include, but are not limited to, dithiophosphinates such as M(S$_2$PR$_2$)$_2$ wherein M is preferably selenium, tellurium, copper or nickel dithiophosphates such as M{S$_2$P(OR)$_2$}$_2$ wherein M is preferably copper, nickel, selenium or tellurium, and dithiocarbamates such as M(S$_2$CNR$_2$)$_2$ wherein M is preferably copper, nickel, selenium or tellurium and those well known in the art. Particularly useful molecular redox amplification elements include metalloboranes, metal xanthates, metal dithiophosphinates, and metal dithiocarbamates.

These molecular redox compositions are used in combination with a metal nuclei catalyst (or a catalyst precursor), as described below, to provide a readable chemical signal resulting from the catalytic redox reaction. Such reactions may occur at room temperature, or at temperatures up to 200° C. depending on the specific chemical composition comprising the molecular amplification element. More details of molecular redox compositions are provided, for example, in U.S. Pat. No. 4,188,218 (Gysling) that describes metal xanthates such as tellurium xanthates, and U.S. Pat. No. 3,505,093 that describes metalloboranes, these disclosures incorporated herein by reference in their entirety.

Dye-Forming High Gain Redox Amplification Systems

A dye precursor (such as a leuco dye) that is reducible or oxidizable can be used as part of the amplification chemistry in combination with a reducing agent or oxidizing agent, depending upon the nature of the dye precursor. The product of such catalytic chemical amplification reactions is a dye which can be read visually or instrumentally (e.g., measurement of optical density or of fluorescence, for example).

A leuco dye is a chemical species that can undergo a reaction, such as a redox reaction or pH change to produce a dye. A leuco dye is a precursor species to a dye.

Reducible Dye Precursors or Leuco Dyes

Examples of such compounds which are reducible include tetrazolium salts and leucophthalocyanines that can be incorporated into the analytical detection formulations and methods disclosed herein in combination with a suitable reducing agent and catalyst (or catalyst precursor). Upon catalytic redox reaction a chemical signal is produced by the dye product of the reaction (e.g., a formazan or phthalocyanine dye, respectively).

Useful reducing agents for this system include hydrazine (and its derivatives), amine boranes, phosphite boranes, arsine boranes, phosphine boranes, stibine boranes, boronium salts, salts of hydroborate ions such as BH$_4^-$, B$_3$H$_8^-$ etc., cyanoborohydride ion and of hypophosphite. Useful catalysts (or catalyst precursors) include the metal nuclei described below and the binary compounds noted above.

Oxidizable Leuco Dye Systems

In another embodiment described herein, redox amplification chemistry containing an oxidizable leuco dye in combination with an oxidizing agent, such as a peroxide can be useful. Useful oxidizable leuco dyes include those of the triaryl methine class, including, for example Leucomalachite Green, Leuco Crystal Violet, and Leucoberberlin Blue. Peroxides useful in this type of signal generating system include hydrogen peroxide and organic peroxides. Other oxidizable leuco dyes and oxidizing agents known to those skilled in the art can also be used in this embodiment.

Catalysts (or catalyst precursors) useful in this type of signal generating redox system include the metal nuclei and metal binary nuclei (for example metal sulfides, selenides, tellurides, phosphides and borides) described below as well as various metal ions such as Mn (II), Co (II) and Fe (II). Mn (II), for example, is a useful catalyst for peroxide oxidation as described in U.S. Pat. No. 4,057,427. These metal ion catalysts such as Mn (II) or other useful metal ions function as homogeneous catalysts or supported homogeneous catalysts for such oxidation reactions.

Peroxide High Gain Redox Amplification Chemistry

Another catalytic amplification chemistry can include what is known in the photographic art as a color developing agent (e.g., a chemical reducing agent), and a peroxide (either hydrogen peroxide or an organic peroxide chemical oxidizing agent). Color developing agents are compounds that, in oxidized form, will react with what are known in the photographic art as dye forming color couplers. Such color developing agents include, but are not limited to, aminophenols, p-phenylenediamines (especially N,N-dialkyl-p-phenylenediamines) and others which are well known in the art. It may be useful for the color developing agents to have one or more water-solubilizing groups as are known in the art.

Preferred color developing agents include, but are not limited to, N,N-diethyl p-phenylenediamine sulfate (KODAK Color Developing Agent CD-2), 4-amino-3-methyl-N-(2-methane sulfonamidoethyl)aniline sulfate, 4-(N-ethyl-N-β-hydroxyethylamino)-2-methylaniline sulfate (KODAK Color Developing Agent CD-4), p-hydroxyethylethylaminoaniline sulfate, 4-(N-ethyl-N-2-methanesulfonylaminoethyl)-2-methylphenylenediamine sesquisulfate (KODAK Color Developing Agent CD-3), 4-(N-ethyl-N-2-methanesulfonylaminoethyl)-2-methylphenylenediamine sesquisulfate, and others readily apparent to one skilled in the art.

Peroxides useful in this imaging system include hydrogen peroxide and organic peroxides.

Catalysts (or catalyst precursors) useful in these chemical elements include heterogeneous catalysts such as metals and metal binary compounds (for example sulfides, selenides, tellurides, phosphides and borides), as well as homogeneous catalysts comprising various metal ions such as Mn (II), Co (II) and Fe (II).

Tellurium High Gain Redox Amplification System

Another useful catalytic redox amplification chemistry of the present invention includes a tellurium (II) or tellurium (IV) compound in combination with a suitable reducing agent and metal nuclei catalyst or catalyst precursor. A range of tellurium (IV) compounds is useful as oxidizing agents. Especially useful tellurium (IV) compounds are organotellurium (IV) compounds of the general formula: R$_n$TeX$_{4-n}$ (I)

wherein R is independently, in each occurrence, a substituted or unsubstituted alkyl, substituted or unsubstituted aryl or substituted or unsubstituted acyl group, X is a halide, pseudohalide or carboxylate, and n is 1 to 4. The halides (X) include Cl, Br and I. Pseudohalides include ligands functionally similar to halides, such as OCN, SCN, SeCN, TeCN or $N_3$. Typical carboxylates include $O_2CCH_3$ (acetate), $O_2CCF_3$ (trifluoroacetate) and $O_2CPh$ (benzoate). Ph in all occurrences in this application designates substituted or unsubstituted phenyl. R includes, but is not limited to, substituted and unsubstituted alkyl groups (preferably those containing from 1 to 10 carbon atoms), substituted and unsubstituted aryl groups (preferably containing from 6 to 10 carbon atoms, such as phenyl and naphthyl), and substituted and unsubstituted acyl groups, preferably containing from 1 to 11 carbon atoms, such as formyl, acetyl, propanoyl, butanoyl, benzoyl, α- or β-naphthoyl, acetylacetonato, or the like).

In one particularly preferred form the formula I compound is $TeX_2R_2$ (II) wherein X is Cl or Br, R is an alkyl or aryl group as defined above or $CH_2C(O)Ar$, or $(R)_2$ (both occurrences of R taken together) is $—CH_2C(O)CR_1R_2C(O)CH_2—$. Ar is preferably phenyl, p-anisyl or o-anisyl. $R_1$ and $R_2$ are preferably hydrogen or methyl. Useful compounds of this type include $Te(p-CH_3O—C_6H_4)_3Cl$, $Te(C_6H_4-p-OCH_3)_2Cl_2$, $TeCl_2[CH_2C(O)-o-OCH_3—C_6H_4]_2$, $TeCl_2[CH_2C(O)—C_6H_5]_2$, $TeCl_2[CH_2C(O)-p-CH_3O—C_6H_4]_2$, $TeBr_2[CH_2C_6H_5]_2$, $TeCl_2[CH_2C(O)C(CH_3)_2C(O)CH_2]$ and $TeCl_2[CH_2C(O)CH_2C(O)CH_2]$.

The described complexes of tellurium (IV) generally have a coordination number of four although compounds containing an organic group R that is functionalized with one or more Lewis base substituents may have coordination numbers greater than 4 [for example the organotellurium-(IV) chelate, $TeCl_3$-(2,6-diacetylpyridine-C,N,O] that has a coordination number of 6, as taught in U.S. Pat. No. 4,239,846.

The term organotellurium (IV) compound as used herein is intended to include any type of bonding or complexing mechanism which enables the resulting material to provide oxidizing agent properties and the described oxidation-reduction amplification element combination when combined with a reducing agent, such as an organic reducing agent. These redox elements can be introduced as a solution or incorporated in a polymeric matrix coated on a suitable substrate. In some cases the exact bonding of the described tellurium (IV) compound is not fully understood. Accordingly, the term "compound" is intended to include salts and other forms of bonding in the desired oxidation-reduction image precursor combination. The term organotellurium compound also is intended to include neutral complexes or salts of non-neutral complexes.

The selection of an optimum organotellurium (IV) compound for an amplification element of this invention will depend upon such factors as the particular reducing agent in the amplification element, processing conditions, and the like.

Especially useful organotellurium (IV) oxidizing agents include $TeX_2(CH_2C_6H_5)_2$ (wherein X is Cl, Br, I or acetyloxy), $TeCl_2[CH_2C(O)Ar]_2$ (wherein Ar is phenyl, p-anisyl or o-anisyl), and $TeX_2 [CH_2C(O)CR_1R_2C(O)CH_2]$ [wherein X is halide, pseudohalide or carboxylate as described above, and $R_1$ and $R_2$ are H, alkyl (such as methyl) or aryl].

Tellurium (II) coordination compounds containing 1,1-dithio ligands are also useful as oxidants in this invention. Such compounds include, but are not limited to, those having the following formula: $Te(S_2X)_2$ wherein X is COR (xanthates, and R is an alkyl or aryl group as defined above), $CNR_2$ (dithiocarbamates, and R is an alkyl or aryl group as defined above), $RP_2$ (dithiophosphinates, and R is an alkyl or aryl group as defined above), $P(OR)_2$ (dithiophosphates, and R is an alkyl or aryl group as defined above), or CR (dithiocarboxylates, and R is an alkyl or aryl group as defined above). These and other useful Te(II) compounds have been described for example in U.S. Pat. No. 4,251,623 (Gysling) and U.S. Pat. No. 4,152,155 (Lelental et al).

Reducing Agents

The redox formulation described herein can comprise a variety of reducing agents. These reducing agents can be organic reducing agents, inorganic reducing agents or combinations of both, with organic reducing agents being preferred. Reducing agents that are especially useful are typically silver halide developing agents and borane type reducing agents. Examples of useful reducing agents include, but are not limited to, phenolic reducing agents (such as polyhydroxybenzenes, including, for instance, hydroquinone, alkyl-substituted hydroquinones, including tertiary butyl hydroquinone, methyl hydroquinone, 2,5-dimethylhydroquinone and 2,6-dimethylhydroquinone; catechols and pyrogallols; chloro-substituted hydroquinones, such as chlorohydroquinone or dichlorohydroquinone; alkoxy-substituted hydroquinones, such as methoxyhydroquinone or ethoxyhydroquinone; aminophenol reducing agents such as 2,4-diaminophenols and methylaminophenols), ascorbic acid reducing agents (such as ascorbic acid, ascorbic acid ketals and ascorbic acid derivatives), hydroxylamine reducing agents, 3-pyrazolidone reducing agents (such as 1-phenyl-3-pyrazolidone and 4-methyl-4-hydroxymethyl 1-phenyl-3-pyrazolidone), reductone reducing agents (such as 2-hydroxy-5-methyl-3-piperidino 2 cyclopentenone), sulfonamidophenol reducing agents and others readily apparent to one skilled in the art. Inorganic reducing agents can include borane type reductants such as $LBH_3$ where L=an amine or organophosphine (for example $PPh_3BH_3$, $Me_2HNBH_3$, $Me_3NBH_3$, $Et_3NBH_3$, and pyridine$BH_3$), and hydroborate salts, including $BH_4^{-1}$ salts such as $KBH_4$, $Et_4NBH_4$ and $[(PPh_3)_2N]BH_4$ and $K[B_3H_8]$, $Cs[B_9H_{14}]$, $Na_2[B_{10}H_{10}]$, and related hydroborate salts as described in U.S. Pat. No. 3,406,019 (Muetterties). Useful inorganic reducing agents also include, for example, those described in U.S. Pat. No. 3,598,587. Combinations of reducing agents can be employed, if desired.

A broad range of concentrations of the reducing agents is useful in the formulations of the invention. The optimum concentration will depend upon such factors, as the particular composition, amplification reaction temperature, desired readable signal, and the like. Typically a concentration of from about 0.01 to about 10 moles of reducing agent per mole of oxidizing agent is employed in the redox amplification formulation, preferably a concentration of from about 0.1 to about 5 moles of reducing agent per mole of oxidizing agent is used.

In another embodiment the chemical amplification system is incorporated in a polymeric matrix in the form of a layer on a suitable substrate such as a paper or polymeric film base and the analyte, labeled with the catalyst or catalyst precursor, is applied to the system containing the chemical amplification element and the chemical amplification reaction occurs spontaneously at room temperature or by heating this system comprising the analyte and the selective binding agent containing the catalyst or catalyst precursor to a temperature up to 200° C.

A preferred high gain chemical amplification formulation comprises a reducible or oxidizable leuco dye, and an oxidizing or a reducing agent, respectively, that upon contact with catalyst or catalyst precursor is capable of catalytic generation of a corresponding dye.

The leuco dye and an oxidizing or a reducing agent are dissolved or dispersed in water or an organic solvent or a polymeric matrix. An organic solvent can be an alcohol, for example methanol, or an ester.

A particularly preferred high gain amplification process is based on the formation of a formazan dye or a metalized formazan dye via catalytic reduction of a corresponding tetrazolium salt by the reducing agent that does not spontaneously reduce said tetrazolium salt, said reducing agent being selected from the group consisting of hydrazines, amine boranes, phosphite boranes, arsine boranes, phosphine boranes, stibine boranes, boronium salts, hydroborate ions such as $BH_4^{-1}$, $B_3H_8^{-1}$, cyanoborohydride ion etc. and hypophosphite.

Another preferred high gain amplification process is based on the formation of a phthalocyanine dye via catalytic reduction of a leucophthalocyanine dye by the reducing agent that does not spontaneously reduce said leucophthalocyanine dye, said reducing agent being selected from the group consisting of amine boranes, phosphite boranes, pyridine boranes, phosphine boranes, stibine boranes, boronium salts, borohydride ion, and cyanoborohydride ion.

Another most preferred high gain amplification process is based on formation of a nickel phthalocyanine dye using palladium metal catalyst or palladium organometallic or coordination compound catalyst precursor, nickel leucophthalocyanine and dimethylamine borane reducing agent.

The most preferred high gain amplification process is based on formation of a formazan dye from the corresponding tetrazolium salt using palladium metal catalyst or palladium salt, organometallic or coordination compound catalyst precursor. A preferred redox combination is 2,3,5-triphenyl-2H-tetrazolium chloride leuco dye, and a hydrazine or an amine borane such as dimethylamine borane reducing agent.

The most preferred redox combination is a tetrazolium salt that produces on chemical reduction, a water soluble formazan dye such as 2,3-Bis-(2-methoxy-4-nitro-5-sulfophenyl)-2H-tetrazolium-5-carboxanilide sodium salt (XTT) leuco dye, and a hydrazine or an amine borane such as dimethylamine borane reducing agent capable of catalytic generation of a corresponding water-soluble formazan dye.

The formation of a water-soluble formazan dye signal is useful in ELISA-format bioassays where the assay signal generated by the redox amplification formulation is measured by optical spectrophotometry. For assays involving visualization of analytes/biomarkers on solid tissue sample a water insoluble dye or a metal is preferred as the product of the redox amplification reaction.

Method

The detection methods of this invention can be used for a broad spectrum of biological materials such as, serum, toxins, nucleic acid, antigens, sugars, lipids, cells and viruses, as well as polysaccharides, lipopolysaccharides, proteins, glycoproteins, lipoproteins, nucleoproteins, peptides, oligonucleotides, specifically antibodies, immunoglobulins, albumin, hemoglobin, coagulation factors, peptide and protein hormones (insulin, gonadotropin, somatotropins), non-peptide hormones, interleukins, interferons and other cytokines, peptides comprising a tumor-specific epitope, cells (red blood cells), cell-surface molecules (CD antigens integrins, cell receptors), microorganisms (viruses, bacteria, parasites, molds, fungi) and their fragments, components or products, small organic molecules (digoxin, heroin, cocaine, morphine, mescaline, lysergic acid, tetrahydrocannabinol, cannabinol, steroids, pentamidine, biotin), genes, viral RNA or DNA, bacterial DNA, fungal DNA, mammalian DNA, cDNA, mRNA, RNA and DNA fragments, oligonucleotides, synthetic oligonucleotides modified oligonucleotides, single- and double-stranded nucleic acids, and natural and synthetic nucleic acids in biological fluids (serum, plasma, blood, saliva, urine), cells, cell lysates, tissues, pathogens, and organic chemicals or peptides, etc.

A method of this invention provides means to detect and quantify the presence of selected analyte using the nanoparticles conjugated with specific binding reactant which contain a metal catalyst or a metal catalyst precursor using a high-gain visualization chemical reaction redox amplification reaction. The metal catalyst or metal catalyst precursor is capable of promoting such chemical amplification reactions leading to the formation of a reaction product, such as a dye, a metal or a material having luminescing (e.g., fluorescing or phosphorescing) properties. The formation of the product of this high-gain catalytic amplification reaction is subsequently detected and quantified by using an appropriate instrumental analytical technique including colorimetric, fluorimetric, or chemilumimetric methods. The specific assay signal measurement technique will be determined by the chemical nature of the redox amplification reaction product (e.g., a dye, or a metal), as well as the phase of the product (e.g., solution or solid).

A method disclosed herein detects and quantifies the presence of a target analyte of interest by a high gain redox chemical amplification reaction having an amplification factor of $10^7$ to $10^9$. The method includes reacting marking nanoparticles coupled to a metal catalyst or a metal catalyst precursor and a biospecific binding reactant that is selectively reactive with the target analyte of interest. The method includes selectively forming a first reaction product of the metal catalyst or the metal catalyst precursor contained in a reaction mixture. The reaction mixture is separated into two or more fractions (for example by an appropriate chromatographic separation technique). The target analyte of interest is detected and quantified by subjecting said first reaction product present in at least one of said fractions to a high gain redox chemical amplification formulation including an oxidizing agent and a reducing agent to produce a second reaction product in the form of a dye or metal wherein the dye or metal is formed in a reaction catalyzed by said first reaction product. An appropriate signal produced by the second dye or metal product is measured to determine the concentration of the target analyte.

Enzyme-linked immunosorbant assay (ELISA) is a test that uses antibodies and color change to identify a substance, Conventional ELISA is a well-established assay routinely practiced in wet-labs. This type of biochemistry assay uses a solid-phase enzyme immunoassay (EIA) to detect the presence of a substance, usually an antigen, in a liquid sample or wet sample. The ELISA has been used as a diagnostic tool in medicine and plant pathology, as well as a quality-control check in various industries.

In an ELISA, antigens from the sample are attached to a surface. Then, a further specific antibody is applied over the surface so it can bind to the antigen. This antibody is linked to an enzyme, and, in the final step, a substance containing the enzyme's substrate is added. The subsequent enzyme-catalyzed reaction produces a detectable signal, most commonly an organic dye which is quantified by optical spectrophotometry.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are not specifically bound. After the final wash step, the plate is developed by adding an enzymatic substrate to produce a visible signal, which indicates the quantity of antigen in the sample. The present disclosure allows amplification to provide the detectable signal using catalysis by a metal rather than by an enzyme as in conventional ELISA bioassays.

Bioassay Kit

A diagnostic kit is a collection of supplies and equipment for use in performing a diagnostic bioassay and can be put together for the purpose (by an individual or organization, for instance), or purchased complete. There is a wide variation in the contents of diagnostic bioassay kits based on the knowledge and experience of those putting it together, the differing bioassay requirements of the area where it may be used, and variations in legislation or regulation in a given area.

A diagnostic kit for ultrasensitive bioassay of this invention can comprise a dispersion comprising a plurality of catalytic marking nanoparticles which contain a metal catalyst or a metal catalyst precursor, and are conjugated to least one biospecific binding reactant, a dispersing medium and a dispersing aid or dispersion stabilizing agent, a high gain redox chemical amplification formulation comprising a leuco dye or a reducible metal complex, a reducing agent, an ELISA plate and the ELISA bioassay reagents (e.g., capture and detection antibodies specific for the target disease biomarker, the blocking agent and buffers).

EXAMPLES

Figure 1:
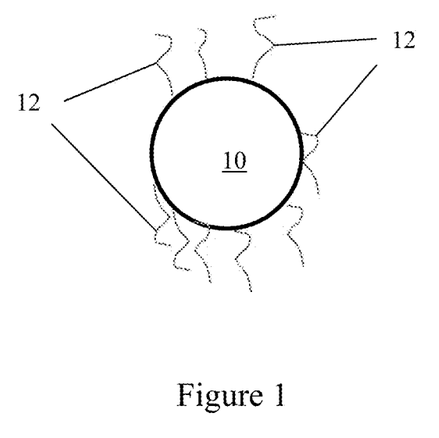
FIG. 1 cross-sectional view of an embodiment of a catalytic nanoparticle for ultrasensitive bioassays of the present invention.
Figure 2:
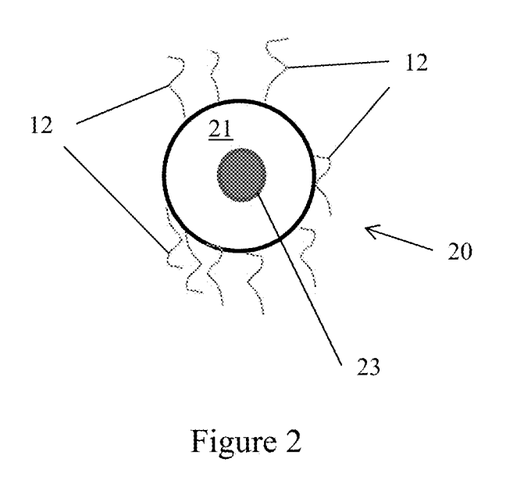
FIG. 2 cross-sectional view of an embodiment of a catalytic nanoparticle for ultrasensitive bioassays of the present invention.

Shown in FIGS. 1 and 2 are embodiments of the invention. In FIG. 1 a catalytic nanoparticle is shown. The particle 10 is a water-insoluble, water swellable polymer containing a metal catalyst or metal catalyst precursor immobilized within the volume of the particle 10 and/or on the surface of the particle 10. A biospecific binding reagent 12 is conjugated with the nanoparticle 10. A plurality of the nanoparticles 10 containing the metal catalyst or metal catalyst precursor conjugated with a specific binding reagent 12 are dispersed in a dispersing medium.

In FIG. 2 a catalytic nanoparticle of an embodiment described herein is shown. The particle 20 has a water-insoluble, water swellable polymer shell 21 containing a metal catalyst or metal catalyst precursor within the volume shell 21 and/or on the surface of the shell 21. The particle 20 includes an inner core 23 that can be chemically/physically inert organic, including polymeric, inorganic or organic-inorganic composite material or can be a water insoluble but water-swellable polymer. A biospecific binding reagent 12 is conjugated with the nanoparticle 20. A plurality of the nanoparticles 20 conjugated with a specific binding reagent 12 are dispersed in a dispersing medium.

It will be appreciated that variants of the above-disclosed embodiments and other features and functions or alternatives thereof, may be combined into other different systems or applications. Various presently unforeseen or unanticipated alternatives, modifications, variations, or improvements therein may be subsequently made by those skilled in the art which are also encompassed by the following claims.

What is claimed is:

1. A composition for bioassay applications comprising:
a plurality of dispersible polymeric nanoparticles having a particle size less than 500 nm, wherein the polymeric nanoparticles comprise a water-insoluble, water-swellable polymer, wherein the polymeric nanoparticles contain a metal catalyst precursor, the metal catalyst precursor capable of being chemically reduced by a reducing agent to produce an active catalyst for an assay signal generation reaction, wherein the metal catalyst precursor is selected from the group consisting of: $K_2[M(C_2O_4)_2]$, $PdCl_2$, $K_3[CO(C_2O_4)_3]$, $K_2[MCl_4]$, $[Et_4N]_2[MCl_4]$, $[M_4(PR_3)_2Cl_2]$, $[M'(acac)_2(CO)_2]$; $[Co(NH_3)_5N_3]Cl_2$, $[Pd[P(C_6H_5)_3]_2(C_2O_4)]$, $\{Cu[P(OCH_3)_3]_4\}B(C_6H_5)_4$, $\{Cu[P(OCH_3)_3]_2BH_3CN\}_2$, $\{Cu[Sb(C_6H_5)_3]_3Cl\}$ and $[Cu(ethylenediamine)_2][B(C_6H_5)_4]_2$, wherein M is Pd or Pt, wherein R is alkyl or aryl, wherein M' is Rh or Ir, and acac is acetylacetonate;
at least one biospecific binding reactant that is selectively reactive with a target analyte; and
a dispersing medium.

2. The composition according to claim 1, wherein the water-insoluble, water-swellable polymer is selected from the group consisting of: crosslinked gelatin, albumin, agar-agar, gum arabic, alginic acid, synthetic materials and polyelectrolytes.

3. The composition according to claim 2, wherein the synthetic materials are selected from the group consisting of: acidic, water-insoluble, water-swellable polymers having functional groups that are capable of acting as acids.

4. The composition according to claim 2, wherein the synthetic materials are selected from the group consisting of: basic, water-insoluble, water-swellable polymers having functional groups that are capable of acting as bases.

5. The composition according to claim 4, wherein the basic, water-insoluble, water-swellable polymers is selected from the group consisting of: polyacrylamides, polyvinyl alcohols, ethylene maleic anhydride copolymer, polyvinylethers, polyacrylic acids, polyvinylpyrrolidones, polyvinylmorpholines, natural based polysaccharides, carboxymethyl celluloses, carboxymethyl starches, hydroxypropyl celluloses, algins, alginates, carrageenans, acrylic grafted starches, acrylic grafted celluloses and synthetic polypeptides.

6. The composition according to claim 2, wherein the polyelectrolytes are selected from the group consisting of: poly(allylamine hydrochloride), poly(diallydimethylammonium chloride), polyacrylic acid, poly(methacrylic acid), poly(sodium styrene sulfonate), and poly(2-acrylamido-2-methyl-1-propane sulphonic acid).

7. The composition according to claim 1, wherein the at least one biospecific binding reactant is selected from the group consisting of an antibody, an antigen, an epitope, a receptor ligand, a specific binding protein, avidin, streptavidin, biotin, a nucleic acid, and a peptide.

8. The composition according to claim 1, wherein the biospecific binding reactant is conjugated to the polymeric nanoparticles by adsorption, covalent coupling, grafting or solid phase synthesis.

9. The composition according to of claim 1, wherein the polymeric nanoparticles comprise a core-shell structure, the shell comprising the water-insoluble, water-swellable polymer, the metal catalyst precursor within a volume of the shell and the at least one biospecific binding reactant conjugated to a surface of the shell that is selectively reactive with the target analyte.

10. The composition according to claim 9, wherein the core has a particle size of from about 1 nm to about 500 nm and the shell layer has a thickness of from about 0.5 nm to about 249.5 nm.

11. The composition according to claim 1, wherein the at least one biospecific binding reactant is streptavidin that can selectively react with the target analyte.

12. A composition for bioassay applications comprising:
a plurality of dispersible polymeric nanoparticles having a particle size less than 500 nm, wherein the polymeric nanoparticles comprise a core-shell structure having a water-insoluble, water-swellable polymer as the shell, wherein the core-shell polymeric nanoparticles contain a metal catalyst precursor within a volume of the shell, the metal catalyst precursor capable of being chemically reduced by a reducing agent to produce an active catalyst for an assay signal generation reaction, at least one biospecific binding reactant that is selectively reactive with a target analyte, the at least one biospecific binding reactant is conjugated to a surface of the shell; and
a dispersing medium.

13. The composition according to claim 12, wherein the metal catalyst precursor is selected from the group consisting of: a metal salt, an organometallic compound and a coordination compound having an element selected from the group consisting of copper, silver, gold, nickel, palladium, platinum, manganese, cobalt, rhodium and iridium.

14. The composition according to claim 12, wherein the water-insoluble, water-swellable polymer is selected from the group consisting of: crosslinked gelatin, albumin, agar-agar, gum arabic, alginic acid, synthetic materials and polyelectrolytes.

15. The composition according to claim 14, wherein the synthetic materials are selected from the group consisting of: basic, water-insoluble, water-swellable polymers having functional groups that are capable of acting as bases.

16. The composition according to claim 15, wherein the basic, water-insoluble, water-swellable polymers are selected from the group consisting of: polyacrylamides, polyvinyl alcohols, ethylene maleic anhydride copolymer, polyvinylethers, polyacrylic acids, polyvinylpyrrolidones, polyvinylmorpholines, natural based polysaccharides, carboxymethyl celluloses, carboxymethyl starches, hydroxypropyl celluloses, algins, alginates, carrageenans, acrylic grafted starches, acrylic grafted celluloses and synthetic polypeptides.

17. The composition according to claim 14, wherein the polyelectrolytes are selected from the group consisting of: poly(allylamine hydrochloride), poly(diallydimethylammonium chloride), polyacrylic acid, poly(methacrylic acid), poly(sodium styrene sulfonate), and poly(2-acrylamido-2-methyl-1-propane sulphonic acid).

18. The composition according to claim 12, wherein the at least one biospecific binding reactant is selected from the group consisting of an antibody, an antigen, an epitope, a receptor ligand, a specific binding protein, avidin, streptavidin, biotin, a nucleic acid, and a peptide.

19. The composition according to claim 12, wherein the core has a particle size of from about 1 nm to about 500 nm and the shell layer has a thickness of from about 0.5 nm to about 249.5 nm.

* * * * *